United States Patent [19]

Varum

[11] Patent Number: 4,998,978
[45] Date of Patent: Mar. 12, 1991

[54] TOOTH CLEANING STRIP

[76] Inventor: Shirley B. Varum, 27775 Williams Canyon Rd., Gaston, Oreg. 97119

[21] Appl. No.: 463,268

[22] Filed: Jan. 10, 1990

[51] Int. Cl.$^5$ .............................................. A61C 15/00
[52] U.S. Cl. ...................................... 132/321; 433/142
[58] Field of Search ................ 433/216, 142; 132/321, 132/322, 323, 324, 325, 329

[56] References Cited

U.S. PATENT DOCUMENTS

| | | | |
|---|---|---|---|
| 718,401 | 1/1903 | Thomas | 132/321 |
| 1,149,376 | 8/1915 | Leonard et al. | 132/323 |
| 1,285,988 | 11/1918 | Gudebrad | 132/323 |
| 1,997,877 | 4/1935 | Spanel | 132/321 |
| 2,771,084 | 11/1956 | Fleming | 132/321 |
| 2,771,085 | 11/1956 | Fleming | 132/321 |
| 2,771,889 | 11/1956 | Fleming | 132/321 |
| 3,491,776 | 1/1970 | Fleming | 132/321 |
| 4,211,330 | 7/1980 | Strock | 132/312 |
| 4,265,258 | 5/1981 | Eaton | 132/321 |
| 4,776,358 | 10/1988 | Lorch | 132/321 |
| 4,817,643 | 4/1989 | Olson | 433/216 |

Primary Examiner—John J. Wilson
Attorney, Agent, or Firm—Eugene M. Eckelman

[57] ABSTRACT

A flat flexible strip has a length by means of which it can be reciprocated longitudinally in rubbing engagement with tooth surfaces. The strip is constructed of crossed strands forming cross ridges in surfaces of the strip that produce a frictional scrubbing engagement against teeth surfaces when the strip is reciprocated longitudinally. Strands can be arranged in a woven pattern or a haphazard pressed pattern. The edges of the strip are reinforced in a non-raveling structure. The strip may be of a width up to about ½ inch and a thickness up to about 4 mls.

2 Claims, 1 Drawing Sheet

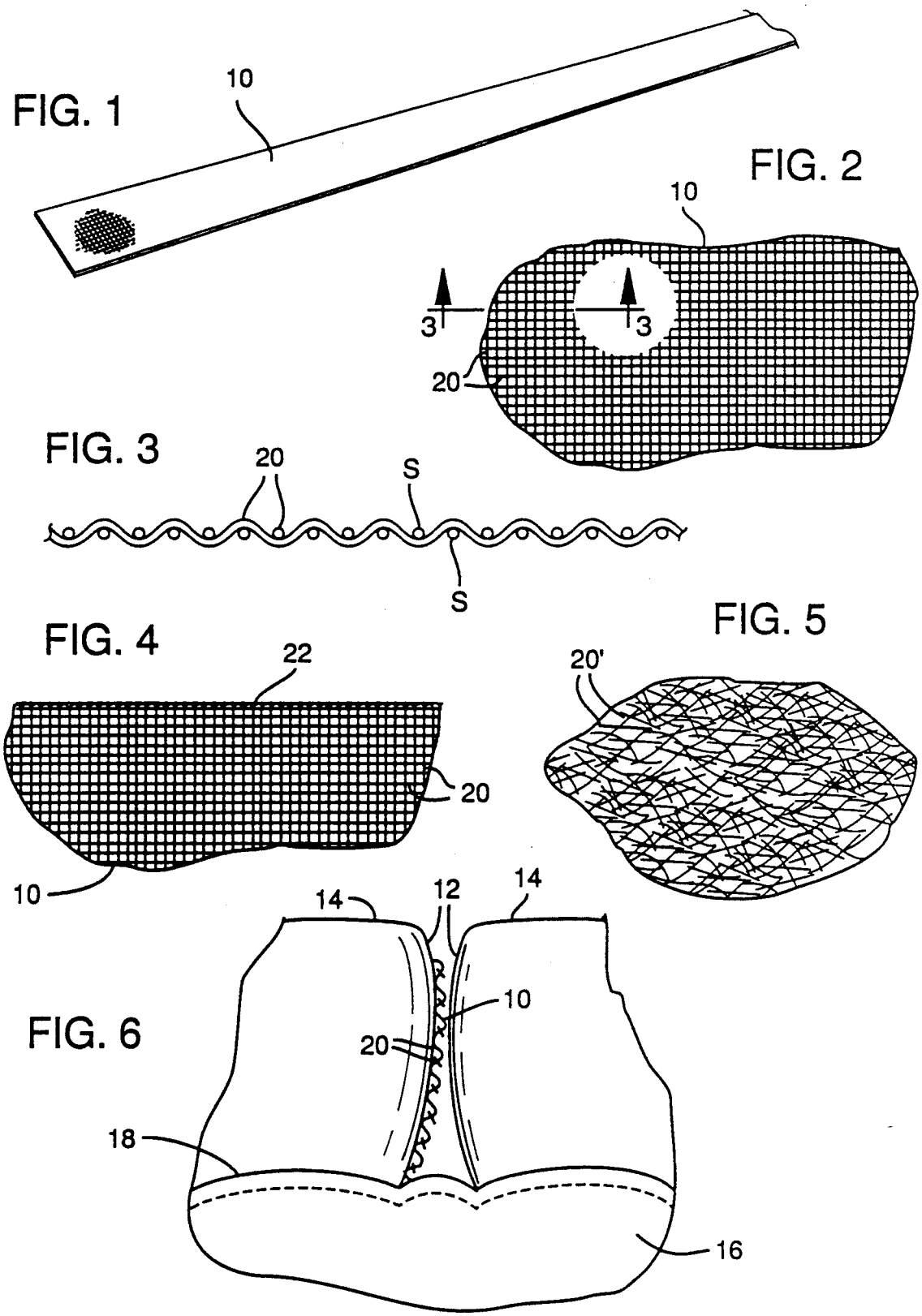

TOOTH CLEANING STRIP

BACKGROUND OF THE INVENTION

Various forms of dental floss have heretofore been provided for cleaning interproximal areas and other areas not accessible by a toothbrush. Such flossing step has been found to be a valuable asset in preventing the formation of plaque and tartar on tooth surfaces. A common type of floss on the market is in the form of a small diameter, smooth surfaced filament that must be rubbed vigorously up and down and lengthwise against the tooth surfaces. A disadvantage of this filament type floss is that it requires considerable time to clean tooth surfaces. Also, it can cut into the gums at the papilla during vigorous flossing. In an attempt to clean the teeth, as well as to satisfy the desires of the public, floss is furnished in various sizes, it is waxed, flavored and widened in ribbon form. In another instance, and as seen in U.S. Patent No. 4,776,358, a tape-type floss has a dentrifice and an adhesive incorporated therein with the advantage that it cleans and polishes the teeth.

SUMMARY OF THE INVENTION

According to the invention and forming a primary objective thereof, a tooth cleaning strip is provided that possesses a novel structure facilitating an improved cleaning function for tooth surfaces.

A more particular object of the invention is to provide a strip type of dental floss that has a crossed strand construction, such as from threads, filaments, fibers, etc. in a structural arrangement that applies an improved scrubbing action to the surface of teeth.

Another object of the invention is to provide a tooth cleaning strip of the type described that is effective in its scrubbing action without damaging the gums.

Still another object is to provide a floss that is inexpensive to manufacture and easy to use.

In carrying out these objectives, the present strip is made up of strands wherein such strands provide cross surface ridges that scrub teeth areas when the strip is worked longitudinally back and forth. The strands are arranged in the strip in patterns that present them angularly or across the longitudinal length of the strip so that the cross ridges formed by the strands provide a scrubbing action on the teeth surfaces. The strip preferably has non-raveling edges that contribute to the structural strength and ease of use without unraveling.

The invention will be better understood and additional objects and advantages will become apparent from the following description taken in connection with the accompanying drawings.

BRIEF DESCRIPTION OF THE DRAWINGS

FIG. 1 is a perspective view of a piece of tooth cleaning strip embodying features of the present invention.

FIG. 2 is a greatly enlarged fragmentary plan view of a piece of the strip which uses a woven construction of strands.

FIG. 3 is an enlarged fragmentary sectional view taken on the line 3—3 of FIG. 2.

FIG. 4 is an enlarged plan view of the strip of FIG. 1 and illustrating an edge construction thereof.

FIG. 5 is an enlarged fragmentary plan view of a strip using a pressed fiber-type strand; and FIG. 6 is an elevational view showing use of the present strip in relation to teeth areas.

DETAILED DESCRIPTION OF PREFERRED EMBODIMENTS

The invention comprises a thin strip or tape 10, FIG. 1, constructed of a suitable flexible material, to be described, and a width and thickness, also to be described, that can be readily forced into interproximal areas and can readily remove plaque and other matter that cling to the teeth.

With reference to FIG. 6, the invention performs the function of dental floss in that it is used to clean the interproximal areas 12 of teeth 14. The numeral 16 designates the gums and the numeral 18 designates the papilla. The invention accomplishes an improved cleaning of the teeth surfaces above the gums as well as teeth surfaces between the teeth and under the papilla.

As a feature of the invention, this strip has crossed strand construction 20 wherein, upon longitudinal reciprocating movement of the strip, an efficient friction cleaning is accomplished. With particular reference to FIGS. 2 and 3, the strands 20 of the strip comprise a woven arrangement made up of interlaced threads or filaments extending at right angles to each other. Viewed along the surfaces of the strip in section, FIG. 3, it is apparent that these woven strips inherently form a ridged surface S on each side formed by the cross strands. This ridged surface will frictionally engage and remove plaque and other matter on the teeth when rubbed thereagainst. By pulling the strip back and forth and at the same time forcing it against the surfaces being engaged, an effective cleaning is accomplished.

With reference to FIG. 4, it is preferred that the strip have non-raveling edges 22. Such unraveling edges reinforce these edges not only to prevent unraveling but also to form a somewhat rigid leading edge for efficient edge movement into interproximal areas.

FIG. 6 shows the present strip 10 in engagement in the interproximal area of two teeth. As stated, cleaning is accomplished by back and forth and pressured contact with the teeth. Downward movement relative to the gums will also move a bottom non-raveling edge 22 into the area of the papilla 18 for complete cleaning.

Other constructions of the strip are within the concept of the invention. For example, as shown in FIG. 5, the crossed 20' strands may comprise fibers laid and pressed in a haphazard manner in a thin fabric. These strands form an efficient frictional rubbing surface similar to the woven material of FIG. 1 in that in such haphazard arrangement of the fibers there are adequate cross strands to form the friction surface.

The material used for the present strip can be cloth, plastic, or any other material capable of construction with crossed strands for frictionally removing plaque. The strip can be up to about ½ inch in width, with a preferred width of ⅛ to ¼ inch. The thickness can be up to about 4 mls, with a preferred thickness of about 3 mls. In all cases, improved oral hygiene can be accomplished. If necessary, removal of the strip from tight interproximal areas can be lengthwise through the opening existing between the teeth at the gum line.

The present strip can be treated with fluoride or other medication. It also can have a polish or whitening agent thereon and can be flavored or colored. Furthermore, it can be treated with a stiffening agent to keep it flat. It is easy to use and to grip, and due to its width covers a large area at a time, thus saving time for flossing. It can be supplied in individual strips or in rolls. Another use of the present strip and forming it within the range of dimensions given above, dentists can use the strip to test smoothness and spacing of teeth inlays and crowns.

It is to be understood that the form of my invention herein shown and described is to be taken as a preferred example of the same and that various changes in the shape, size and arrangement of parts may be resorted to without departing from the spirit of my invention, or the scope of the subjoined claims.

Having thus described my invention, I claim:

1. A tooth cleaning strip comprising:
 a flat, single layer, flexible strip having opposite surfaces, side edges, and a length by means of which it can be reciprocated longitudinally in contoured rubbing engagement with toothed surfaces in the interproximal areas thereof,
 said strip being constructed of strands crossed at right angles in a woven structure and forming cross ridges in said surfaces that are capable of producing a frictional scrubbing engagement against tooth surfaces when the strip is reciprocated longitudinally against the tooth surfaces,
 a non-raveling portion along at least one of said side edges,
 said strip having a width up to about ½ inch and a thickness up to about 4 mls.

2. The tooth cleaning strip of claim 1 wherein said strip has a width of from approximately ⅛ inch to ¼ inch and a thickness of 3 mls.

* * * * *

UNITED STATES PATENT AND TRADEMARK OFFICE
CERTIFICATE OF CORRECTION

PATENT NO.  :   4,998,978
DATED       :   March 12, 1991
INVENTOR(S) :   SHIRLEY B. VARNUM It is certified that error appears in the above-identified patent and that said Letters Patent is hereby corrected as shown below:

On Title page, Item [75], correct the spelling of applicant's name to --Shirley B. Varnum--.

Signed and Sealed this

Fifteenth Day of December, 1992

Attest:

DOUGLAS B. COMER

*Attesting Officer*          *Acting Commissioner of Patents and Trademarks*